US00PP35313P2

(12) United States Plant Patent
Kappel

(10) Patent No.: US PP35,313 P2
(45) Date of Patent: Aug. 15, 2023

(54) CHERRY TREE NAMED 'SPC495'

(50) Latin Name: *Prunus avium*
Varietal Denomination: SPC495

(71) Applicant: Her Majesty the Queen in Right of Canada as Represented by the Minister of Agriculture and Agri-Food, Ottawa (CA)

(72) Inventor: Frank Kappel, Kanata (CA)

(73) Assignee: HER MAJESTY THE QUEEN IN RIGHT OF CANADA AS REPRESENTED BY THE MINISTER OF AGRICULTURE AND AGRI-FOOD, Ottawa (CA)

( * ) Notice: Subject to any disclaimer, the term of this patent is extended or adjusted under 35 U.S.C. 154(b) by 0 days.

(21) Appl. No.: 17/953,127

(22) Filed: Sep. 26, 2022

Related U.S. Application Data

(60) Provisional application No. 63/248,734, filed on Sep. 27, 2021.

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./156, 180, 181
See application file for complete search history.

*Primary Examiner* — Karen M Redden
(74) *Attorney, Agent, or Firm* — Penny J. Aguirre

(57) ABSTRACT

A new cultivar of *Prunus avium* tree named 'SPC495' that is characterized by its very late fruit harvest, its flowers that are self-fertile, its large fruit with a desirable appearance, its fruit with a low level of natural splitting, and its good storage potential in regular air MAP bag.

2 Drawing Sheets

Botanical classification: *Prunus avium.*

Variety denomination: 'SPC495'.

BACKGROUND OF THE INVENTION

The present invention relates to a new and distinct cultivar of *Prunus avium* and will be referred to hereafter by its cultivar name, 'SPC495'. 'SPC495' is a new cultivar of sweet cherry tree grown for fruit production.

The new cultivar of *Prunus* arose from a breeding program conducted by the Inventor at a research center in Summerland, B.C., Canada with the goal of developing a new cultivar of cherry tree with improved fruit appearance, taste, firmness, flesh texture, productivity, precocity, harvest timing, and split resistance with improved tree quality and disease resistance.

The new cultivar arose from open pollination of '13S2009' (U.S. Plant Pat. No. 20,551) in 2000. The male parent is therefore unknown. The Inventor selected 'SPC495' as a single unique plant amongst the resulting seedlings in 2009.

Asexual propagation of the new cultivar was first accomplished by budding onto Mazzard (not patented) rootstock under the direction of the Inventor in Summerland, B.C., Canada in 2009. Asexual propagation by budding has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'SPC495' as a unique cultivar of cherry tree.

1. 'SPC495' exhibits a very late fruit harvest.
2. 'SPC495' exhibits flowers that are self-fertile.
3. 'SPC495' exhibits large fruit with a desirable appearance.
4. 'SPC495' exhibits fruit with a low level of natural splitting.
5. 'SPC495' exhibits good storage potential in regular air MAP (Modified Atmosphere packaging) bag.

The female parent, '13S2009', is similar to 'SPC495' in having fruit with excellent eating attributes and dark red in color and flowers that are self-fertile. The female parent differs from 'SPC495' in having fruit that are larger in size, less firm, a higher rate of natural spitting, and an earlier harvest time, and a later blooming period. 'SPC495' can be most closely compared to the cultivar 'Sweetheart' (not patented). 'Sweetheart' is similar to 'SPC495' in being self-fertile and having fruit with low susceptibility to natural splitting. 'Sweetheart' differs from 'SPC495' in having fruits that are smaller in size with less natural splitting and a much earlier harvest period.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure included but may not be limited to a website listing by ANFIC Fruit Variety Catalogue (as a trial variety).

BRIEF DESCRIPTION OF THE DRAWINGS

The accompanying color photograph illustrates the overall appearance and distinct characteristics of 'SPC495' on a 15-year-old tree as grown in a trial plot in Summerland, B.C., Canada.

The photograph in FIG. 1 provides a view of a cluster of fruit of 'SPC495'.

Figure 1:
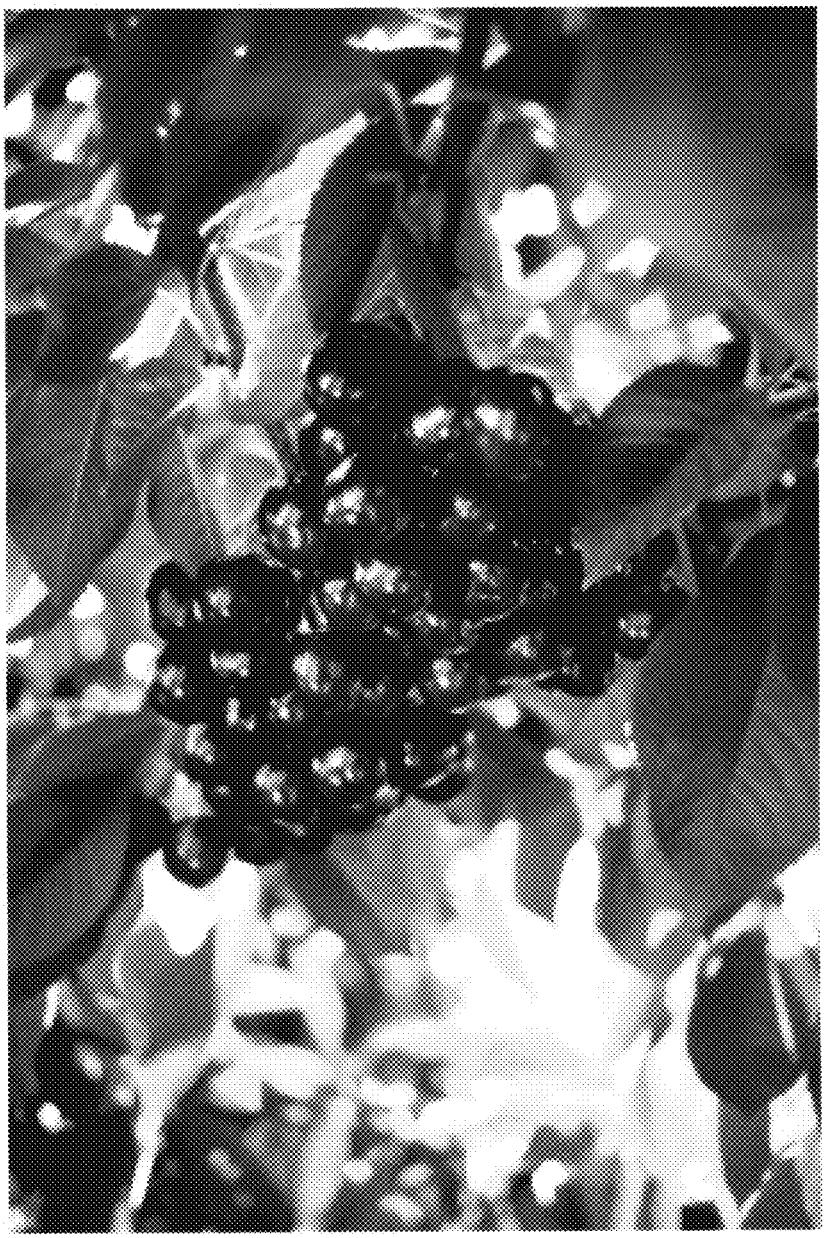
Figure 2:
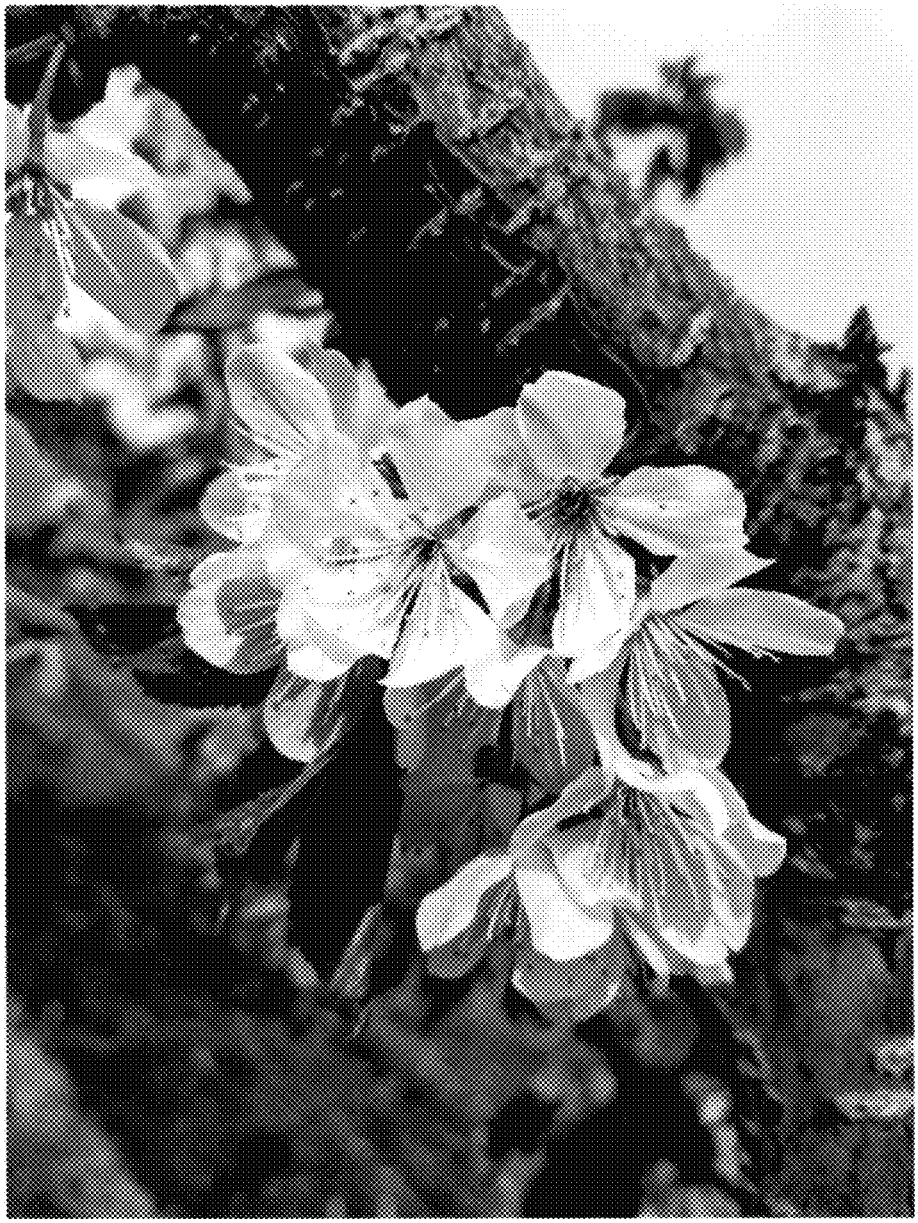

The photograph in FIG. 2 provides a close-up view of the flowers of 'SPC495'.

The colors in the photograph are as close as possible with the digital photography techniques available, the color values cited in the detailed botanical description accurately describe the colors of the cherry tree.

DETAILED BOTANICAL DESCRIPTION

The following is a detailed description of 15-year-old trees as grown in a trial plot in Summerland, B.C., Canada. The phenotype of the new cultivar may vary with variations in environmental, climatic, and cultural conditions, as it has not been tested under all possible environmental conditions. The color determination is in accordance with the 2001 Colour Chart of The Royal Horticultural Society, London, England, except where general color terms of ordinary dictionary significance are used.

General description:

*Plant type.*—Deciduous fruit bearing tree.

*Plant habit.*—Upright and spreading with medium crown density.

*Height and spread.*—Reaches about 4 m in height and about 2.4 m in spread when grown on Mazzard rootstock in a 2.4 m by 4.5 m training pattern.

*Cold hardiness.*—To at least U.S.D.A. Zone 6.

*Diseases and pests.*—No susceptibility or resistance to diseases or pests has been observed.

*Root description.*—Fibrous, freely branched.

*Propagation.*—Budding onto rootstock.

*Growth rate.*—Moderate to vigorous.

Trunk description:

*Size of trunk.*—22 cm in diameter measured 30 cm above soil level.

*Bark color.*—187A, lenticels 197D.

*Bark texture.*—Young stems; smooth, with slightly raised bumps, older bark; slightly rough.

Description of dormant shoots (one year-old):

*Pubescence.*—None.

*Shoot size.*—Average of 72.9 cm in length and 10.6 mm in width at basal end.

*Anthocyanin presence.*—None.

*Thickness of shoot at center of middle internode.*—Medium; average of 7.7 mm.

*Bark color.*—165A, lenticels 163D, larger branches can have short longitudinal striations of 188D.

*Shoot angle.*—Erect.

*Lenticels.*—Numerous.

*Branch internode length.*—Medium.

*Vegetative buds.*—Large in size; 5.5 mm in length and 3.2 mm width, conical to round in shape, adpressed to held slightly out from shoot, support is medium.

Description of growing shoots:

*Color of growing tip of shoot.*—144B with very light tinge of 187A.

*Pubescence of shoots tip.*—None.

*Anthocyanin presence.*—Very light.

Foliage description:

*Leaf shape.*—Elliptic with tendency to cuneate.

*Leaf division.*—Simple.

*Leaf base.*—Acute.

*Leaf apex.*—Acuminate at very tip.

*Leaf fragrance.*—None.

*Leaf burst.*—Early in the beginning of full flowering.

*Leaf venation.*—Pinnate, not prominent, same as leaf color with the midrib on upper surface and lower surface, 145C.

*Leaf margins.*—Biserrate.

*Leaf arrangement.*—Alternate.

*Leaf aspect.*—Slightly cupped longitudinally.

*Leaf attachment.*—Petiolate.

*Leaf surface.*—Glabrous and slightly glossy on upper surface and weakly to moderately pubescent on lower surface.

*Leaf size.*—Mature leaves average 14.5 cm in length and 7.1 cm in width.

*Leaf internodes.*—Average of 5.0 cm.

*Leaf color.*—Newly expanded leaves upper and lower surface; 174A with 139C around the spine, veins, and serration tips, mature leaves upper surface; 137A, mature leaves lower surface; 137C.

*Petioles.*—Average of 3.6 cm in length and 2.2 mm in width, front of petiole 187A, back of petiole 144B in color, glabrous surface.

Inflorescence description:

*Blooming period.*—Early-mid in sweet cherry bloom season in Summerland BC, Canada.

*Inflorescence type.*—Clusters of single flowers.

*Lastingness of inflorescence.*—Average of 5 days.

*Flower fragrance.*—Faint.

*Flower quantity.*—About 3 per inflorescence.

*Flower type.*—Rotate, corolla above an elongated calyx with stamens and pistil extended.

*Flower size.*—Average of 3.8 cm in diameter.

*Calyx.*—Comprised of sepals fused into an ovoid base with un-fused portions spreading at apex.

*Sepals.*—5, upper and lower surface; 146D in color with 25% of both surfaces tinged with anthocyanin 187A, glabrous surface, 7.2 mm in length with un-fused portions about 4.5 mm in width, entire glandular margin, attenuate apex, fused base.

*Petals.*—5, broadly elliptic in shape, un-fused, thin and papery substance, smooth margin, acute base, emarginate apex, about 1.74 cm in length and 1.34 cm in width, both surfaces 155D in color.

*Pedicels.*—Average of 2.11 cm in length, 1.3 mm in width, 146D in color, glabrous surface.

*Rachis.*—Glabrous surface, flowers lightly compacted with whorled arrangement.

Reproductive organs:

*Gynoecium.*—Pistil; 1, about 1.7 cm in length and extending beyond perianth, style; 152C in color, stigma and style; 1.38 cm in length, stigma is about <1 mm in diameter and 152D in color, ovary; superior, glabrous and 144B in color, nectarines; 2, kidney shaped, 22A and 46A in color.

*Androecium.*—Stamens; 33, base adnate to calyx, filaments; 155D in color, about 1.42 cm in length and <1 mm in width, anthers; 164B in color, dorsifixed, about 1.42 cm in length and in <1 mm width, pollen; abundant in quantity, 163B in color.

*Fertility.*—Self-fertile.

Fruit description:

*Fruit type.*—Drupe.

*Fruit shape.*—Kidney to cordate.

*Fruit apex.*—Flat with low susceptibility to rain induced cracking.

*Fruit size.*—Large, 2.7 cm in length and 2.4 cm in width.

*Fruit firmness.*—Firm.

*Fruit set.*—Medium-heavy.

*Fruit stalk.*—Medium in length and thickness; 4.6 cm in length and 0.9 mm in width, surface glabrous and fine with longitudinal striations, color 145B.

*Fruit bearing.*—Intermediate precocious.

*No. of fruit per cluster.*—1 to 2.

*Skin color.*—187A when ripe with a light colored dots 183D.

*Harvest date.*—Very late; after August $10^{th}$ in Summerland, BC, Canada.

*Skin surface.*—Glossy.

*Skin suture.*—Moderate prominence.

*Flesh color.*—180D and 46A.

*Juice.*—Moderate juiciness and 46A in color.

*Flesh texture.*—Fleshy, moderately juicy.

*Apex end.*—Size medium and color 166D.

*Flavor.*—Medium sweetness.

*Fruit use.*—Fresh fruit.

*Weight.*—10.2 g.

*Brix.*—19%.

*Acidity.*—10.5 TA (ml NaOH).

*Storage life.*—Up to +6 weeks at 1° C.).

*Productivity.*—18,000 to 20,000 lbs. per acre when grown on Mazzard rootstock.

*Seeds.*—1 stone per berry, 165B in color, medium in size; average of 1.15 cm in length and 1.03 cm in width and medium in comparison to fruit, shape; lateral view is symmetrical, slight semi-adherent to flesh, front view is broadly elliptic, basal view is round, keel is strongly developed.

It is claimed:

1. A new and distinct cultivar of *Prunus* tree named 'SPC495' as herein illustrated and described.

* * * * *